United States Patent
Lin et al.

(10) Patent No.: US 10,271,800 B2
(45) Date of Patent: Apr. 30, 2019

(54) WEARABLE ELECTRONIC DEVICE AND EMERGENCY METHOD THEREOF

(71) Applicants: LITE-ON ELECTRONICS (GUANGZHOU) LIMITED, Guangzhou (CN); Lite-On Technology Corporation, Taipei (TW)

(72) Inventors: Shiang-Hua Lin, Taipei (TW); Kuang-Yao Liao, Taipei (TW); Ping-Mao Lee, Taipei (TW); Wei-Chun Liao, Taipei (TW)

(73) Assignees: LITE-ON ELECTRONICS (GUANGZHOU) LIMITED, Guangzhou (CN); Lite-On Technology Corporation, Taipei (TW)

( * ) Notice: Subject to any disclaimer, the term of this patent is extended or adjusted under 35 U.S.C. 154(b) by 0 days.

(21) Appl. No.: 15/790,081

(22) Filed: Oct. 23, 2017

(65) Prior Publication Data
US 2018/0235551 A1 Aug. 23, 2018

(30) Foreign Application Priority Data
Feb. 23, 2017 (CN) .......................... 2017 1 0100863

(51) Int. Cl.
*A61B 5/00* (2006.01)
*G08B 21/04* (2006.01)

(52) U.S. Cl.
CPC ............ *A61B 5/746* (2013.01); *A61B 5/0015* (2013.01); *A61B 5/681* (2013.01); *A61B 5/6843* (2013.01); *A61B 5/7282* (2013.01); *A61B 5/7445* (2013.01); *G08B 21/0453* (2013.01); *A61B 2560/0209* (2013.01)

(58) Field of Classification Search
None
See application file for complete search history.

(56) References Cited

U.S. PATENT DOCUMENTS

| | | | | |
|---|---|---|---|---|
| 4,120,296 A | * | 10/1978 | Prinz ...................... | A61B 5/024 600/503 |
| 4,252,128 A | * | 2/1981 | Kane .................. | A61B 5/02444 40/640 |
| 4,280,506 A | * | 7/1981 | Zurcher ............. | A61B 5/02241 600/503 |
| 4,305,401 A | * | 12/1981 | Reissmueller ..... | A61B 5/02241 600/503 |
| 4,338,950 A | * | 7/1982 | Barlow, Jr. ............ | A61B 5/024 600/500 |

(Continued)

FOREIGN PATENT DOCUMENTS

| CN | 203988003 | 12/2014 |
|---|---|---|
| CN | 104739401 | 7/2015 |

(Continued)

*Primary Examiner* — Curtis J King
(74) *Attorney, Agent, or Firm* — JCIPRNET

(57) ABSTRACT

A wearable electronic device and an emergency method thereof are provided. The wearable electronic device includes a host and a strap. The host senses physiological information of a user by using a sensor. When the physiological information is determined as being abnormal, the host sends an enabling signal to the strap by a transmitting coil to enable the strap. After the strap is enabled, a warning light module displays a warning message based on the enabling signal.

7 Claims, 2 Drawing Sheets

(56) References Cited

U.S. PATENT DOCUMENTS

| | | | | |
|---|---|---|---|---|
| 4,402,560 A * | 9/1983 | Swainbank | A61N 1/14 | 439/37 |
| 4,407,295 A * | 10/1983 | Steuer | A61B 5/02438 | 600/483 |
| 4,409,983 A * | 10/1983 | Albert | A61B 5/02438 | 600/502 |
| 5,499,398 A * | 3/1996 | Kudoh | H01Q 1/273 | 455/290 |
| 5,810,736 A * | 9/1998 | Pail | A61B 5/681 | 600/480 |
| 5,906,582 A * | 5/1999 | Kondo | A61B 5/222 | 600/479 |
| 6,063,036 A * | 5/2000 | Li | A61B 5/02438 | 600/500 |
| 6,130,616 A * | 10/2000 | Sizemore | G08B 13/149 | 340/573.1 |
| 6,198,951 B1 * | 3/2001 | Kosuda | A61B 5/02416 | 600/323 |
| 6,281,800 B1 * | 8/2001 | Sizemore | G08B 13/149 | 340/573.1 |
| 6,314,058 B1 * | 11/2001 | Lee | A61B 5/02141 | 368/10 |
| 6,400,974 B1 * | 6/2002 | Lesho | A61B 5/0031 | 600/345 |
| 9,292,008 B1 * | 3/2016 | Ahamed | G06F 1/163 | |
| 2003/0011469 A1 * | 1/2003 | Bush | A41D 19/0157 | 340/326 |
| 2004/0162534 A1 * | 8/2004 | Powers | A45D 34/00 | 604/310 |
| 2006/0047327 A1 * | 3/2006 | Colvin | A61B 5/076 | 607/60 |
| 2006/0253010 A1 * | 11/2006 | Brady | G16H 40/67 | 600/324 |
| 2008/0262364 A1 * | 10/2008 | Aarts | A61B 5/021 | 600/509 |
| 2010/0163591 A1 * | 7/2010 | Stutz | A45F 3/04 | 224/579 |
| 2011/0205057 A1 * | 8/2011 | Sizemore | G01S 19/17 | 340/568.6 |
| 2012/0221254 A1 * | 8/2012 | Kateraas | A61B 5/02055 | 702/19 |
| 2013/0207813 A1 * | 8/2013 | Ng | G08B 5/004 | 340/815.45 |
| 2013/0310658 A1 * | 11/2013 | Ricks | A61B 5/1118 | 600/301 |
| 2014/0073486 A1 * | 3/2014 | Ahmed | A61B 5/02405 | 482/9 |
| 2014/0275817 A1 * | 9/2014 | Script | A61B 5/01 | 600/301 |
| 2014/0378853 A1 * | 12/2014 | McKinney | A61B 5/02438 | 600/509 |
| 2015/0105221 A1 * | 4/2015 | Roush | G06Q 50/22 | 482/8 |
| 2015/0272458 A1 * | 10/2015 | Magniez | A61B 5/02438 | 600/479 |
| 2015/0313542 A1 * | 11/2015 | Goldberg | A61B 5/0205 | 600/384 |
| 2015/0341901 A1 * | 11/2015 | Ryu | H04M 1/72569 | 455/458 |
| 2016/0174857 A1 * | 6/2016 | Eggers | G06F 19/3418 | 600/301 |
| 2016/0192526 A1 * | 6/2016 | Gao | G06F 1/163 | 361/679.01 |
| 2016/0203701 A1 * | 7/2016 | Woodard | G08B 25/016 | 340/573.1 |
| 2016/0249864 A1 * | 9/2016 | Kang | A61B 5/02438 | 340/870.07 |
| 2016/0310085 A1 * | 10/2016 | Delia | A61B 5/746 | |
| 2017/0086741 A1 * | 3/2017 | Bly | A61B 5/6826 | |
| 2017/0095171 A1 * | 4/2017 | Park | A61B 5/0022 | |
| 2017/0188668 A1 * | 7/2017 | Watterson | A44C 5/0015 | |
| 2018/0070840 A1 * | 3/2018 | Cronin | A61B 5/02438 | |
| 2018/0184920 A1 * | 7/2018 | Rabinovich | A61B 5/02108 | |

FOREIGN PATENT DOCUMENTS

| | | |
|---|---|---|
| CN | 105005194 | 10/2015 |
| CN | 105595986 | 5/2016 |

* cited by examiner

WEARABLE ELECTRONIC DEVICE AND EMERGENCY METHOD THEREOF

CROSS-REFERENCE TO RELATED APPLICATION

This application claims the priority benefit of Chinese application serial no. 201710100863.X, filed on Feb. 23, 2017. The entirety of the above-mentioned patent application is hereby incorporated by reference herein and made a part of this specification.

BACKGROUND

Field of the Invention

The invention relates to a wearable electronic device and more particularly, to a wearable electronic device combined with an emergency mechanism.

Description of Related Art

Generally, health wristbands are designed on demand for waterproofing, low cost and light weight, and thus, a lightweight small-size screen is preferred in an occasion of choosing a panel. However, at present, the health wristbands, besides monitoring physiological signal detection, are gradually in demand for emergent help when emergent physiological alerts happen.

However, two major issues will be encountered when a space of a wristband body is designed. First, the screen of the wristband body is too small, such that an emergent signal with a large range and sufficient brightness cannot be provided. Second, if a warning indicator is additionally required, the space of the body becomes insufficient. Therefore, the two major issues would result in conflicts in the design of the watch body. For example, the size and the thickness of the appearance would be increased if the aforementioned issues are forcibly added into the design.

SUMMARY

The invention provides a wearable electronic device and an emergency method thereof where a warning light module is disposed on a strap outside a host, thereby increasing a visibility of a warning message.

According to an embodiment of the invention, a wearable electronic device including a host and a strap is provided. The host includes a transmitting coil, a sensor and a power supply device. The sensor senses physiological information of a user. The power supply device is coupled to the sensor and the transmitting coil and supplies power to the host for the host to operate. The strap includes a receiving coil and a warning light module and is detachably assembled to the host. The receiving coil is coupled with the transmitting coil. The warning light module is coupled to the receiving coil. In a condition that the host determines the physiological information as being abnormal by the sensor, the host transmits an enabling signal to the strap to enable the strap by the transmitting coil. In a condition that the strap is enabled, the warning light module displays a warning message based on the enabling signal.

In an embodiment of the invention, the host further includes a power manager and an encoder. The strap further includes a decoder. The power manager is coupled to the power supply device. The encoder is coupled to the power manager and the sensor, and forms the enabling signal by carrying an emergent signal as a carrier on a power signal in the condition that the sensor determines the physiological information as being abnormal. The decoder is coupled to the receiving coil and decodes the enabling signal to obtain the emergent signal. The warning light module displays the warning message based on the emergent signal.

In an embodiment of the invention, the wearable electronic device is a watch, the host is a watch body, and the strap is a detachable watchstrap.

In an embodiment of the invention, the strap further includes a microprocessor. The microprocessor is coupled between the decoder and the warning light module, and converts the emergent signal into the warning message of the warning light module after receiving the emergent signal from the decoder.

In an embodiment of the invention, the strap includes a connection portion and is connected with the host through the connection portion.

In an embodiment of the invention, the receiving coil is accommodated in the connection portion, and the connection portion is made of a shielding material.

In an embodiment of the invention, the warning light module is a light emitting diode (LED) module.

According to an embodiment of the invention, an emergency method of a wearable electronic device including a host and a strap is provided. The emergency method includes: sensing physiological information of a user by the host; when the physiological information is determined as being abnormal by the host, transmitting an enabling signal to the strap to enable the strap by the host; and in a condition that the strap is enabled, displaying a warning message based on the enabling signal by a warning light module.

Based on the above, with the sensor built in the wearable electronic device, energy and messages can be transmitted through a wireless power to be presented on the warning light module of the strap, so as to achieve an emergency emergent function. The warning light module disposed on the strap can contribute to increasing visibility of the warning message.

In order to make the aforementioned and other features and advantages of the invention more comprehensible, several embodiments accompanied with figures are described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF EMBODIMENTS

Figure 1:
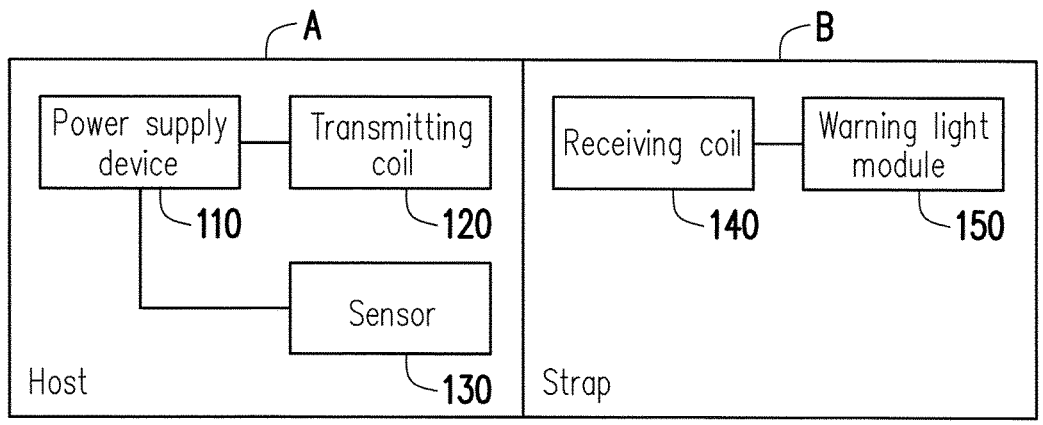
FIG. 1 is a block diagram illustrating a wearable electronic device according to an embodiment of the invention.

FIG. 1 is a block diagram illustrating a wearable electronic device according to an embodiment of the invention. Referring to FIG. 1, a wearable electronic device 10 includes a host A and a strap B. The strap B is detachably assembled to the host. In the present embodiment, the wearable electronic device 10 is, for example, a smart watch, the host A is a watch body, and the strap B is a detachable watchstrap.

The host A of the present embodiment, as illustrated, includes a power supply device 110, a transmitting coil 120 and a sensor 130. The host A is also certainly integrated with an operation unit, a storage unit, a positioning unit, a transmitting unit and/or other specific functional elements. However, other functional elements are not the focus of the invention and thus, are omitted from the illustration. The power supply device110 is coupled to the transmitting coil 120 and the sensor 130. The power supply device110 is configured to supply power to the host A, such that each element of the host A can be operated. The sensor 130 may be configured to sense a user's physiological information, which includes, for example, personal information of heartbeat, pulse, blood pressure, blood oxygen, temperature, respiration and so on.

The strap B is not installed with any battery module and thus, is in a power-off state before the transmitting coil 120 transmits an enabling signal thereto. The strap B includes a receiving coil 140 and a warning light module 150. The warning light module 150 is, for example, a light emitting diode (LED) module. The receiving coil 140 is coupled with the transmitting coil 120. For example, the receiving coil 140 and the transmitting coil 120 use electromagnetic induction coils, and thus, the transmitting coil 120 may transmit energy to the receiving coil 140 by utilizing induction coupling. The warning light module 150 is coupled to the receiving coil 140.

In a condition that the host A determines the physiological information as being abnormal, the host A transmits an enabling signal to the strap B by the transmitting coil 120 to enable the strap B. For example, the enabling signal includes a power signal and an emergent signal. When the strap B receives the enabling signal, the elements of the strap B may utilize the enabling signal as a power signal to operate. In the meanwhile, the warning light module 150 displays a warning message based on the emergent signal.

Additionally, in other embodiments, in a condition that the host A is separated from the strap B, the host A may further be connected with a docking station. For example, the receiving coil 140 and the warning light module 150 are installed in the docking station. In the condition that the host A determines the physiological information sensed by the sensor as being abnormal, the host A transmits the enabling signal to the docking station by the transmitting coil 120, such that the warning light module 150 of the docking station displays the warning message based on the enabling signal. Regarding the docking station, it may be embodied as a monitoring medical equipment or an electronic emergency instrument in a hospital. In this condition, the host A may correspondingly transmit the emergent signal included in the enabling signal to the monitoring medical equipment or the electronic emergency instrument, such that the medical staffs may take medical practices, such as rescuing treatment or surgery, which construes no limitations to the scope of the invention.

Figure 2:
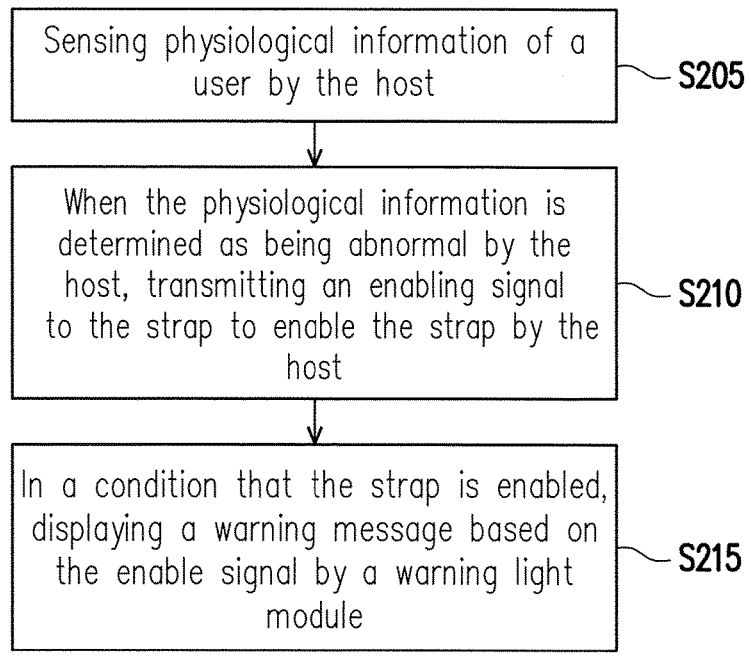
FIG. 2 is a flowchart illustrating an emergency method of a wearable electronic device according to an embodiment of the invention.

FIG. 2 is a flowchart illustrating an emergency method of a wearable electronic device according to an embodiment of the invention. In the present embodiment, when a user wears the wearable electronic device 10, the wearable electronic device 10 may instantly monitor and sense the physiological information of the user.

Referring to FIG. 1 and FIG. 2 simultaneously, in step S205, the physiological information of the user is sensed by the sensor 130 of the host A. Taking the wearable electronic device 10 being a smart watch as an example, the user may wear the wearable electronic device 10 on his/her wrist, such that the sensor 130 installed in the host A may sense the physiological information of the user at any time.

Then, in step S210, when the host A determines the physiological information as being abnormal, the host A transmits the enabling signal to the strap B to enable the strap B. Thereafter, in step S215, in the condition that the strap B is enabled, the strap B displays the warning message based on the enabling signal by the warning light module 150. In this case, an inner side of the strap B is adjacent to the user, and the warning light module 150 is disposed on an outer side of the strap B. In this way, other people around the user may become aware of the warning message when the warning message is displayed by the warning light module 150.

In addition, the warning message displayed on the warning light module 150 may be determined by the host A. When the host A determines that the physiological information represents abnormal, a corresponding emergent signal may be carried on the enabling signal according to the current abnormal state. Another embodiment will be provided below for description in detail.

Figure 3:
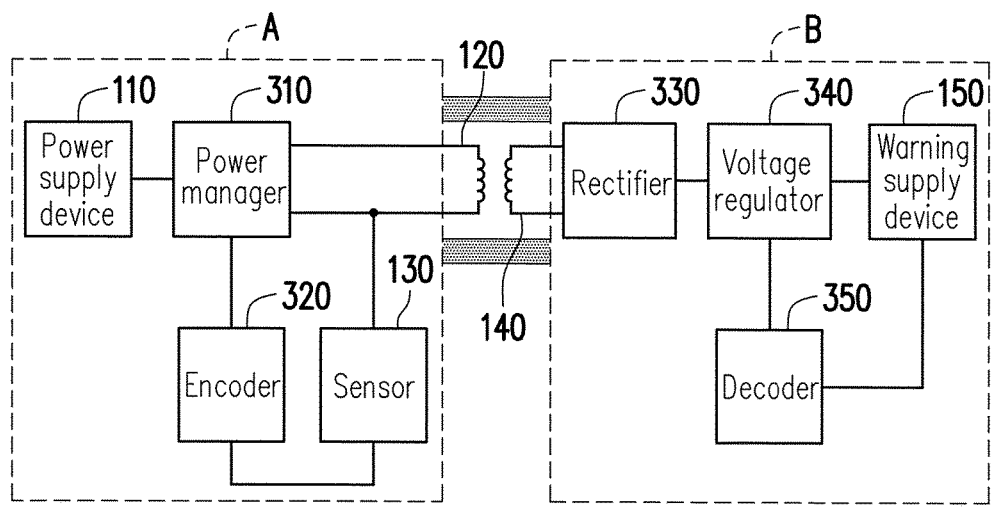
FIG. 3 is a block diagram illustrating a wearable electronic device according to an embodiment of the invention.

FIG. 3 is a block diagram illustrating a wearable electronic device according to an embodiment of the invention. In the present embodiment, the host A of the wearable electronic device 10 may further include a power manager 310 and an encoder 320. The encoder 320 may be employed to carry a corresponding emergent signal on the enabling signal.

The power manager 310 is coupled to the power supply device 110. The encoder 320 is coupled to the power manager 310 to receive the power and is coupled to the sensor 130 to receive the physiological information. The encoder 320 determines whether abnormality occurs to the physiological information sensed by the sensor 130. For example, the encoder 320 may determine whether the sensed heartbeat is lower than a predetermined threshold, or whether the heartbeat has stopped. In the condition that the encoder 320 determines the physiological information sensed by the sensor 130 as being abnormal, the encoder 320 carries the emergent signal on the enabling signal.

Specifically, an AC (alternating current) power (i.e., the enabling signal) has a sine waveform, and thus, the encoder 320 may carry the emergent signal on a peak and a valley of the waveform to transmit the enabling signal by the transmitting coil 120.

The strap B further includes a rectifier 330, a voltage regulator 340 and a decoder 350. The rectifier 330 is a device converting an AC power into a DC (direct current) power to be applied to a power supply device, and is utilized to detect a wireless power signal. The voltage regulator 340 is a device employed to automatically maintain a constant voltage and is operated in corporation with the rectifier 330 to provide a stably output voltage. The decoder 350 is coupled to the receiving coil 140 through the rectifier 330 and the voltage regulator 340. The decoder 350 decodes the enabling signal to obtain the emergent signal.

After the receiving coil 140 receives the enabling signal, the power may be supplied to the entire strap B. In this circumstance, the decoder 350 may decode the enabling signal to retrieve the emergent signal carried on the enabling signal. Thereafter, the decoder 350 drives the warning light module 150 to display the corresponding warning message.

In addition, the strap B may further include a microprocessor (which is not shown). The microprocessor may be coupled between the decoder 350 and the warning light module 150. After receiving the emergent signal from the decoder 350, the microprocessor converts the emergent signal and drives the warning light module 150 to display the warning message.

Figure 4:
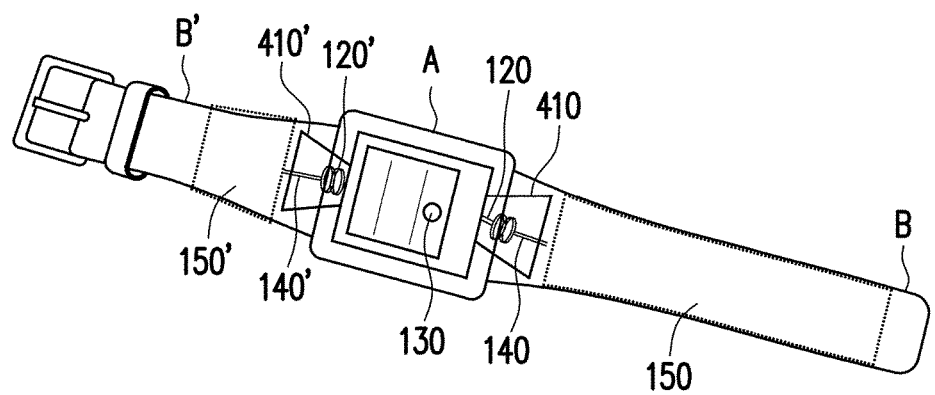
FIG. 4 is a schematic diagram illustrating a watch according to an embodiment of the invention.

FIG. 4 is a schematic diagram illustrating a watch according to an embodiment of the invention. Referring to FIG. 4, a wearable electronic device 40 is, for example, a smart watch, the host A is a watch body, and the strap B is a watchstrap. Two ends of the host A are respectively connected with straps B and B'. The strap B and the strap B' have the same element and functions, and thus, the function of each internal element of the strap B' may refer to the description related to the strap B.

In the present embodiment, the host A functions in the same way as a general electronic watch, and the sensor 130 is installed in the host A. In this circumstance, the illustration of the sensor 130 is only for descriptive convenience, where the sensor 130 is installed inside the host A and is invisible from the appearance. In addition, transmitting coils 120 and 120' are respectively disposed on the two ends, which are connected with the straps B and B', of the host A. The straps B and B' respectively have connection portions 410 and 410' and are connected with the host A respectively through the connection portions 410 and 410'. The connection portions 410 and 410' are installed with connection mechanisms for the straps B and B' to be connected with the host A.

In the strap B, the receiving coil 140 and the transmitting coil 120 are accommodated in the connection portion 410. The connection portion 410 is made of a shielding material, thereby mitigating electromagnetic interference (EMI).

In the present embodiment, the wearable electronic device 40 includes two straps B and B', and thus, different warning messages may be respectively displayed on warning light modules 150 and 150' of the straps B and B'. In addition, different warning messages may be displayed according to different abnormal states of the physiological information. For example, in the two conditions that "the heartbeat is over low" and "the heartbeat has stopped", the carried emergent signals are different, and the decoder 350 displays the corresponding warning message on the warning light module 150 based on the emergent signal.

If the encoder 320 of the host A determines the user's heart beat as being too low, the warning light module 150 of the strap B may display "low pulse" and the warning light module 150' of the strap B' may display "alarm". Additionally, if the encoder 320 of the host A determines that the user's heartbeat has stopped, the warning light module 150 of the strap B may display "cardiac arrest", and the warning light module 150' of the strap B' may display "SOS". However, the above is only illustrated for example, and the invention is not limited thereto.

In light of the foregoing, the transmitting coil is disposed on the host, the warning light module and the receiving coil are disposed on the strap, the power is transmitted through a principle of coupling technology between electromagnetic induction coils, and the emergent signal is transmitted as a carrier. Accordingly, when the host senses an abnormal physiological signal, the power signal and the emergent signal included in the enabling signal can be transmitted to the warning light module of the strap through the coupling between the electromagnetic induction coils, such that the strap can automatically display the warning message to realize the SOS effect.

Moreover, the warning light module is disposed on an outer side of the strap, which can contribute to increasing visibility and increasing a survival probability of a wearer. As the power is transmitted by utilizing the coupling between the electromagnetic induction coils, and thus, the strap does not have to be additionally installed with any battery module, which can avoid the risk of burning or leakage of the battery module. In addition, the power is transmitted by means of electromagnetic induction, the host and the strap are not connected through any physical wire, such that both the host and the strap can be formed with no exposed conductive connection, so as to achieve a waterproofing effect for the host and the strap. Meanwhile, the warning light module can be operated without any external contacts, which can achieve more flexibility in design. Moreover, the strap is designed in a detachable manner, and in an application scenario in a smart watch, the user is allowed to change different watchstraps, which can increase entertainment.

Although the invention has been described with reference to the above embodiments, it will be apparent to one of the ordinary skill in the art that modifications to the described embodiment may be made without departing from the spirit of the invention. Accordingly, the scope of the invention will be defined by the attached claims not by the above detailed descriptions.

What is claimed is:

1. A wearable electronic device, comprising:
   a host, comprising:
   a transmitting coil;
   a sensor, sensing physiological information of a user;
   a power supply device, coupled to the sensor and the transmitting coil, and supplying power to the host;
   a power manager, coupled to the power supply device; and
   an encoder, coupled to the power manager and the sensor, and forming an enabling signal by carrying an emergent signal as a carrier on a power signal in the condition that the physiological information is determined as being abnormal; and
   a strap, detachably assembled to the host, wherein the strap is in a power-off state before the transmitting coil transmits the enabling signal to the strap and the strap comprises:
   a receiving coil, coupled with the transmitting coil; and
   a decoder, coupled to the receiving coil and decoding the enabling signal to obtain the emergent signal;
   a warning light module, coupled to the receiving coil, wherein
   in a condition that the host determines the physiological information as being abnormal, the transmitting coil transmits the enabling signal to the receiving coil of the strap to enable the strap, and
   in a condition that the strap is enabled, the warning light module is activated to operate by utilizing the power signal and the warning light module displays a warning message based on the emergent signal.

2. The wearable electronic device according to claim 1, wherein the wearable electronic device is a watch, the host is a watch body, and the strap is a detachable watchstrap.

3. The wearable electronic device according to claim 1, wherein the strap further comprises:
   a microprocessor, coupled between the decoder and the warning light module, and converting the emergent signal into the warning message of the warning light module after receiving the emergent signal from the decoder.

4. The wearable electronic device according to claim 1, wherein the strap comprises a connection portion and is connected with the host through the connection portion.

5. The wearable electronic device according to claim 4, wherein the receiving coil is accommodated in the connection portion, and the connection portion is made of a shielding material.

6. The wearable electronic device according to claim 1, wherein the warning light module is a light emitting diode (LED) module.

7. An emergency method of a wearable electronic device comprising a host and a strap, the method comprising:
   sensing physiological information of a user by the host;
   when the physiological information is determined as being abnormal by the host, forming an enabling signal by carrying an emergent signal as a carrier on a power signal, and transmitting an enabling signal to the strap to enable the strap by the host, wherein the strap is in a power-off state before the enabling signal is transmitted to the strap; and
   in a condition that the strap is enabled, decoding the enabling signal to obtain the emergent signal, activating a warning light module to operate by utilizing the power signal and displaying a warning message based on the enabling signal by the warning light module.

* * * * *